(12) United States Patent
Shepherd

(10) Patent No.: US 8,800,687 B2
(45) Date of Patent: Aug. 12, 2014

(54) STEERABLE SYSTEM

(71) Applicant: Schlumberger Technology Corporation, Sugar Land, TX (US)

(72) Inventor: Mike Shepherd, Glos (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 13/901,718

(22) Filed: May 24, 2013

(65) Prior Publication Data

US 2013/0299246 A1   Nov. 14, 2013

Related U.S. Application Data

(63) Continuation of application No. 12/808,519, filed as application No. PCT/IB2008/003950 on Dec. 19, 2008, now Pat. No. 8,464,811.

(30) Foreign Application Priority Data

Dec. 19, 2007  (GB) .................................. 0724699.4

(51) Int. Cl.
| | | |
|---|---|---|
| *E21B 7/04* | (2006.01) | |
| *E21B 7/06* | (2006.01) | |
| *B65H 29/60* | (2006.01) | |
| *A61F 13/15* | (2006.01) | |
| *B65H 29/62* | (2006.01) | |

(52) U.S. Cl.
CPC . *E21B 7/06* (2013.01); *E21B 7/067* (2013.01); *B65H 29/60* (2013.01); *A61F 13/15747* (2013.01); *E21B 7/062* (2013.01); *B65H 29/62* (2013.01)

USPC .............................................. 175/61; 175/73

(58) Field of Classification Search
CPC ............ E21B 7/067; E21B 7/06; E21B 7/068
USPC .................... 175/61, 73, 74, 75, 76
See application file for complete search history.

(56) References Cited

U.S. PATENT DOCUMENTS

| | | |
|---|---|---|
| 3,637,032 A | 1/1972 | Jeter |
| 3,667,556 A | 6/1972 | Henderson |
| 3,743,034 A | 7/1973 | Bradley |
| 3,743,043 A | 7/1973 | Gelinas |
| 4,286,676 A | 9/1981 | Nguyen et al. |
| 4,874,688 A | 10/1989 | Ozawa et al. |
| 4,895,214 A | 1/1990 | Schoeffler |
| 4,974,688 A | 12/1990 | Helton |
| 5,316,090 A | 5/1994 | Kuwana et al. |
| 5,467,834 A | 11/1995 | Hughes et al. |
| 5,575,343 A | 11/1996 | Gray |

(Continued)

FOREIGN PATENT DOCUMENTS

| | | |
|---|---|---|
| GB | 2368361 | 5/2002 |
| WO | 01/46549 | 6/2001 |

*Primary Examiner* — Kenneth L Thompson
*Assistant Examiner* — Michael Wills, III
(74) *Attorney, Agent, or Firm* — Chadwick A. Sullivan; Brigitte Echols

(57) ABSTRACT

A steerable system comprises a first rotatable housing, a second rotatable housing connected to the first rotatable housing by an adjustable joint, a cam member held against rotation, in use, and cam follower means cooperable with the cam member and moveable to drive the second rotatable housing for movement relative to the first rotatable housing about the adjustable joint.

14 Claims, 2 Drawing Sheets

(56) References Cited

U.S. PATENT DOCUMENTS

| | | |
|---|---|---|
| 5,875,859 A | 3/1999 | Ikeda et al. |
| 5,899,281 A | 5/1999 | Gynz-Rekowski |
| 5,957,222 A | 9/1999 | Webb et al. |
| 6,092,610 A | 7/2000 | Kosmala et al. |
| 6,158,529 A | 12/2000 | Dorel |
| 6,296,066 B1 | 10/2001 | Terry et al. |
| 6,364,034 B1 | 4/2002 | Schoeffler |
| 6,470,974 B1 | 10/2002 | Moore et al. |
| 6,550,818 B2 | 4/2003 | Robin |
| 6,659,201 B2 * | 12/2003 | Head et al. ............... 175/61 |
| 6,763,900 B2 | 7/2004 | Miszewski |
| 6,769,499 B2 | 8/2004 | Cargill et al. |
| 6,799,646 B1 | 10/2004 | Daigle et al. |
| 6,810,971 B1 | 11/2004 | Sved |
| 6,959,772 B2 | 11/2005 | Stegmaier et al. |
| 7,195,083 B2 * | 3/2007 | Eppink et al. ............. 175/61 |
| 7,234,543 B2 | 6/2007 | Schaaf |
| 7,234,544 B2 | 6/2007 | Kent |
| 7,243,739 B2 | 7/2007 | Rankin, III |
| 7,270,197 B2 | 9/2007 | Puttmann |
| 7,445,059 B1 | 11/2008 | Folgout, Sr. |
| 7,909,117 B2 | 3/2011 | van Steenwyk et al. |
| 2002/0007969 A1 | 1/2002 | Head et al. |
| 2002/0049518 A1 | 4/2002 | Yamamoto |
| 2002/0050410 A1 * | 5/2002 | Miszewski ............... 175/73 |
| 2002/0170751 A1 | 11/2002 | Smith |
| 2003/0051919 A1 * | 3/2003 | Moore et al. ............. 175/73 |
| 2003/0127252 A1 | 7/2003 | Downton et al. |
| 2004/0226747 A1 | 11/2004 | Stegmaier et al. |
| 2004/0262044 A1 * | 12/2004 | Schaaf ..................... 175/61 |
| 2005/0056463 A1 | 3/2005 | Aronstam et al. |
| 2005/0236189 A1 | 10/2005 | Rankin, III |
| 2007/0095575 A1 | 5/2007 | Johnson et al. |
| 2007/0181343 A1 | 8/2007 | Russell et al. |
| 2008/0190665 A1 | 8/2008 | Earles et al. |

* cited by examiner

STEERABLE SYSTEM

CROSS-REFERENCE TO RELATED APPLICATIONS

This is a continuation application of co-pending U.S. patent application Ser. No. 12/808519, filed 16 Dec. 2008, and entitled "STEERABLE SYSTEM," which is hereby incorporated in its entirety for all intents and purposes by this reference.

FIELD OF INVENTION

This invention relates to a steerable system, for example for use in the formation of boreholes.

BACKGROUND

It is commonplace place in the field of borehole formation, for subsequent use in the extraction of hydrocarbons, to use a steerable drilling system to allow control over the path of the borehole. A number of steerable drilling systems are known. For example systems are known in which a bias unit is located close to the drill bit, the bias unit being operable to apply a laterally directed load to the drill bit urging it away from the axis of the borehole in a desired direction. Another form of steerable drilling system includes a bent housing upon which the drill bit is mounted, steering of the system being achieved by controlling the orientation of the bent housing to ensure that the drill bit is pointed in a desired direction. In some arrangements the bent housing is adjustable to control the direction and angle of the drill bit. In other arrangements, the bent housing is of fixed inclination and adjustment of the direction in which the drill bit is pointed is achieved by controlling the angular position of the bent housing.

SUMMARY OF THE INVENTION

It is an object of the invention to provide a steerable system of simple and convenient form.

According to the present invention there is provided a steerable system comprising a first rotatable housing, a second rotatable housing connected to the first rotatable housing by an adjustable joint, a cam member held against rotation. m use, and cam follower means cooperable with the cam member and moveable to drive the second rotatable housing for movement relative to the first rotatable housing about the adjustable joint.

Such an arrangement is advantageous in that the axis of rotation of the second rotatable housing can be held in a substantially fixed position whilst the first and second rotatable housings are rotated. A drill hit carried by the second housing can thus be held in a desired orientation whilst drilling takes place.

Preferably, the first and second rotatable housings are connected to one another in such a manner that rotation of the first housing is transmitted to the second housing. A clutch mechanism, for example in the form of a dog clutch, may be provided to allow rotation of the first housing relative to the second housing.

The cam member is conveniently adjustable to permit adjustment of the orientation of the second housing. The cam member is conveniently in the form of a swash plate. The cam member is preferably mouthed to a sleeve which surrounds at least part of the first housing and which is held against rotation in normal use. For example, the sleeve may comprise as stabiliser. A spherical bearing is preferably provided on the first housing and arranged to support the cam member, One or more linear actuators are preferably provided to drive the cam member for movement relative to the sleeve to adjust its position. The or each linear actuator may be electrically driven or, alternatively, may be hydraulically powered.

The cam followers means preferably comprise follower pistons arranged to be driven by the cam member and moveable to cause movement of drive pistons. The follower pistons are conveniently of smaller diameter than the drive pistons so as to provide a mechanical advantage. Movement of the drive pistons is conveniently transmitted to the second housing by associated push rods.

The push rods are conveniently aligned with the corresponding one of the follower pistons. In such an arrangement the second housing will be inclined relative to the first housing in the same direction as the cam member, but the angle of inclination will be smaller.

BRIEF DESCRIPTION OF THE DRAWINGS

The invention will further be described, by way of example, with reference to the accompanying drawings, in which.

DETAILED DESCRIPTION

Figure 1:
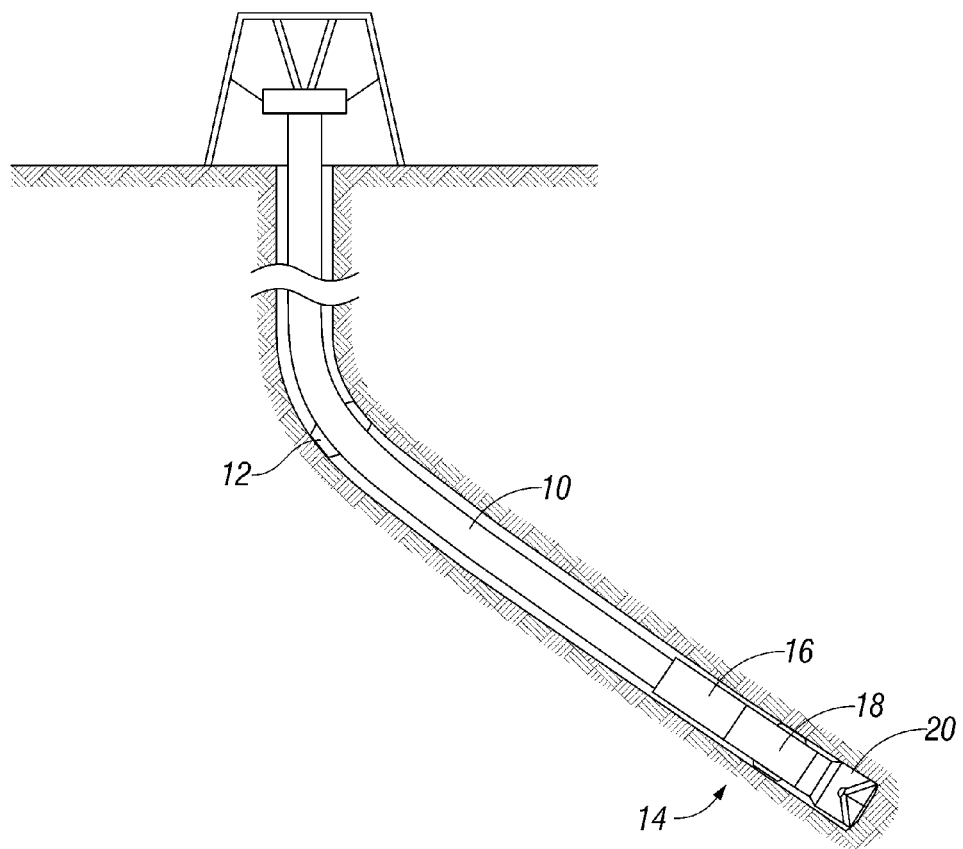
FIG. 1 is a diagrammatic view of a steerable drilling system incorporating the steerable system of one embodiment of the invention.

Referring to the accompanying drawings there is illustrated a steerable dulling system being used in the formation of a borehole. The steerable drilling system comprises a drill string 10 supporting a number of downhole components. The drill string 10 is supported, at the surface, by a rig which serves both a supporting function and also drives the drill string 10 for rotation.

The drill string 10 carries a number of intermediate stabiliser units 12 and, at its lower end, carries a bottom hole assembly 14. The bottom hole assembly 14 includes a downhole motor 16, a steerable system 18, and a drill bit 20. In use, the motor 16 serves to drive the drill bit 20 for rotation. The rotation of the drill bit 20, in combination with weight on bit loadings applied thereto, causes the drill bit 20 to gauge scrape or abrade material from the formation in which the borehole is being formed, extending the borehole.

Although the arrangement illustrated makes use of a downhole motor, arrangements also possible in which the drill bit is driven by the rotation of the drill string.

The steerable system 18 operates to ensure that, whilst drilling is taking place, the drill bit 20 is held in as desired orientation, thus controlling the direction in which the borehole is extended.

Figure 2:
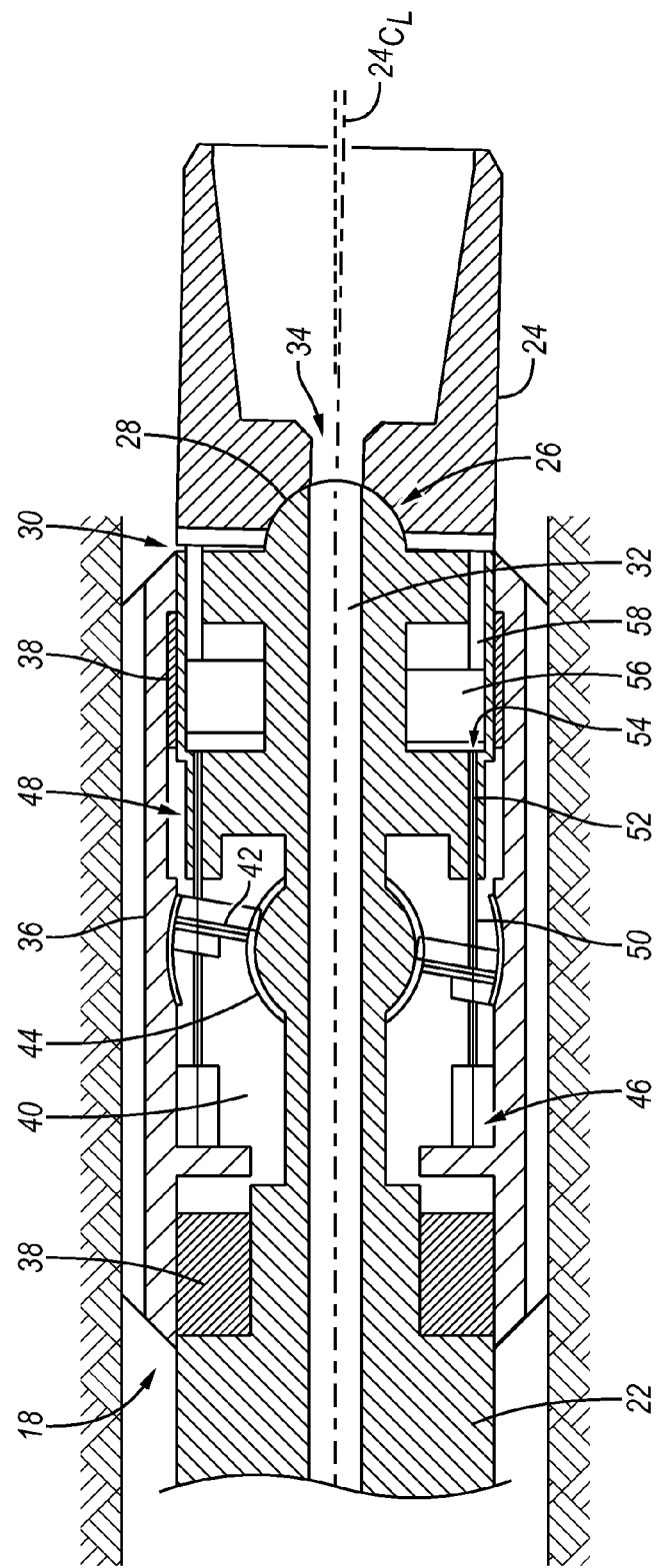
FIG. 2 is an enlarged, sectional view illustrating the steerable system of the drilling system of FIG. 1.

As best illustrated in FIG. 2, the steerable system 18 comprises a first rotatable housing 22 arranged to be connected to the output of the downhole motor 16 so as to be driven for rotation thereby. A second rotatable housing 24 is connected to the first housing 22 by an adjustable joint 26, for example in the form of a universal joint or swivel. The joint 26 includes a part spherical thrust bearing 28 thus permitting the transmission of axially directed loadings from the first housing 22 to the second housing 24, whilst permitting the angle of the axis 24a of the second housing 24 to be adjusted relative to that of the lint housing 22.

A releasable torque transmission arrangement in the form of a dog clutch 30 is provided between the first and second housings 22, 24 such that, when desired, rotation of the first housing 22 about its axis can be transmitted to the second housing 24, release of the dog clutch permitting the first housing 22 to rotate independently of the second housing 24.

An axially extending passage 32 extends through the first housing 22 and the joint 26 to a passage 34 provided in the second housing 24, thus permitting drilling fluid or mud to be supplied through the steerable system 18.

A stabiliser sleeve 36 surrounds part of the first housing 22. The sleeve 36 bears against the wall of the borehole and remains substantially fixed against rotation, in use. The sleeve 36 is mounted to the first housing 22 by bearings 38, which also serve as seals, so as to allow the first housing 22 to rotate whilst the sleeve 36 remains fixed against rotation. The sleeve 36 and first housing 22 together define a chamber 40 within which a cam member in the form of a swash plate 42 is located. The swash plate 42 is keyed or splined to the sleeve 36 such that, in normal use, it is held against rotation. The nature of the connection between the swash plate 42 and the sleeve 36 is such that the angular orientation of the swash plate 42 can be adjusted. A spherical bearing 44 is provided between the inner part of the swash plate 42 and the adjacent part of the first housing 22 to accommodate such movement whilst supporting the swash plate 42. A series of linear actuators 46 are mounted upon the sleeve 36 and engage the swash plate 42, the linear actuators 46 being operable under the control of an appropriate control system (not shown) to adjust the orientation of the awash plate 42 relative to the sleeve 36. The linear actuators 46 may take a range of forms. For example, they could be electrically or electromagnetically actuated, or alternatively they may be hydraulically operated.

The opposite face of the swash plate 42 to that which cooperates with the linear actuators 46 engages a series of cam follower means 48. The cam follower means 48 each comprises a relatively small diameter follower piston 50 which bears against the swash plate 42 and which is reciprocable within a corresponding bore 52 formed in the first housing 22. The bore 52 opens into a larger diameter bore 54 in which a larger diameter drive piston 56 is reciprocable. It will be appreciated that, with such an arrangement, movement of the follower piston 50 causes movement of the associated drive piston 56 in the same direction. The drive piston 56 will move through a smaller distance than the follower piston 50, but is able to apply a larger force by virtue of the mechanical advantage so gained.

A series of push rods 58 bear against the drive pistons 56, transmitting movement thereof to the second housing 24.

In use, in the position illustrated in FIG. 2 it will be appreciated that the swash plate 42 is angled relative to the first housing 22, and that the second housing 24 is tilted relative to the first housing 22 in the same direction as the swash plate 42 but by a smaller angle. From this position, rotation of the first housing 22 due to the operation of the motor 16 causes the follower pistons 50, in turn, to ride up and over the swash plate 42, the follower pistons 50 each being pushed further into the corresponding bores 52 by their movement over the swash plate 42. The movement of the follower pistons 50 is transmitted, by the fluid within the bores 52, 54, to the associated drive pistons 56, extending the push rods 58 and urging the second housing 24 to tilt about the joint 26. The tilting movement of the second housing 24 so achieved drives the push rods 58, and drive and follower pistons 56, 50 on the radially opposite side of the steerable system in the reverse direction towards a retracted position. It will be appreciated that this action ensures that the axis of rotation 24a of the second housing 24 is held substantially fixed in space whilst the first and second housings 22, 24 are rotated. Consequently, the drill bit 20 is held in a desired orientation whilst drilling takes place.

Appropriate adjustment of the position of the swash plate 42 by the linear actuators 46 can be used to adjust the degree of inclination of the second housing 24 relative to the first housing 22 and to adjust the direction or orientation of the axis of rotation 24a of the second housing 24 relative to the first housing 22. It will thus be appreciated that, by appropriate control of the position of the swash plate 42 using the linear actuators 46, the direction of drilling of the steerable drilling system can be controlled.

The mechanical advantage due to the nature of the cam follower means ensures that a sufficiently large magnitude force is available to deflect or tilt the second housing 24 in the desired direction, even when large loading resisting such movement are applied.

It will be appreciated that a wide range of modifications and alterations can be made to the arrangement described hereinbefore without departing from the scope of the invention.

What is claimed is:

1. An apparatus, comprising:
   a motor carried by a drill string within a borehole extending into a subterranean formation;
   a first housing operable to rotate in response to rotation of the motor;
   a second housing operable to rotate in response to rotation of the first housing;
   a bit operable to rotate in response to rotation of the second housing;
   a joint coupled between the first and second housings and operable to orient the bit relative to the motor;
   a sleeve surrounding part of the first housing and rotationally fixed relative to the borehole during rotation of the first housing, the first housing being coupled to the sleeve by bearings permitting rotation of the first housing relative to the sleeve;
   an internal chamber defined by the sleeve and the first housing, wherein the bearings fluidly isolate the internal chamber from the annulus defined between the apparatus and the wall of the borehole;
   a cam member positioned in the internal chamber;
   linear actuators coupled to the sleeve and operable to adjust an orientation of the cam member relative to the sleeve; and
   a cam follower mechanism operable to engage a first surface of the cam member, and wherein the linear actuators are operable to cooperate with a second surface of the cam member opposite the first surface, the cam follower mechanism comprising follower pistons each bearing against the first surface of the cam member and operable to reciprocate within corresponding bores of the first housing.

2. The apparatus of claim 1 wherein the cam member comprises a swash plate.

3. The apparatus of claim 1 wherein the cam member cannot rotate relative to the sleeve.

4. The apparatus of claim 1 further comprising a spherical bearing coupled between the cam member and the first housing.

5. The apparatus of claim 1 wherein the linear actuators are electrically, electromagnetically, or hydraulically operable.

6. The apparatus of claim 1 wherein the bores are first bores, wherein the first housing further comprises second bores of larger diameter than the first bores, and wherein the apparatus further comprises a drive piston in each of the second bores.

7. The apparatus of claim 6 wherein each first bore is in fluid communication with a corresponding one of the second bores, and wherein the drive pistons reciprocate within the corresponding second bores in response to reciprocation of the follower pistons within the corresponding second bores.

8. The apparatus of claim 7 wherein the apparatus further comprises push rods each transmitting movement of a corresponding one of the drive pistons to the second housing.

9. The apparatus of claim 8 wherein adjustment of the orientation of the cam member relative to the sleeve by the linear actuators adjusts an inclination of the second housing relative to the first housing.

10. The apparatus of claim 9 wherein the joint comprises a thrust bearing transmitting axially directed loading from the first housing to the second housing despite the inclination of the second housing relative to the first housing.

11. The apparatus of claim 1 further comprising passages collectively permitting passage of drilling fluid through the first housing, the joint, and the second housing.

12. An apparatus, comprising:
a motor carried by a drill string within a borehole extending into a subterranean formation;
a first housing operable to rotate in response to rotation of the motor;
a second housing operable to rotate in response to rotation of the first housing;
a bit operable to rotate in response to rotation of the second housing;
a joint coupled between the first and second housings and operable to orient the bit relative to the motor;
a sleeve surrounding part of the first housing and rotationally fixed relative to the borehole during rotation of the first housing;
a cam member positioned in an internal chamber defined by the sleeve and the first housing;
linear actuators coupled to the sleeve and operable to adjust an orientation of the cam member relative to the sleeve;
cam follower means operable to engage a first surface of the cam member, wherein the linear actuators are operable to cooperate with a second surface of the cam member opposite the first surface, and wherein the cam follower means comprise follower pistons each bearing against the first surface of the cam member and operable to reciprocate within corresponding first bores of the first housing;
drive pistons in corresponding second bores of the first housing, wherein the second bores are larger in diameter than the first bores, wherein each first bore is in fluid communication with a corresponding one of the second bores, and wherein the drive pistons reciprocate within the corresponding second bores in response to reciprocation of the follower pistons within the corresponding second bores;
push rods each transmitting movement of a corresponding one of the drive pistons to the second housing; and
passages collectively permitting passage of drilling fluid through the first housing, the joint, and the second housing.

13. A method, comprising:
conveying an apparatus on a drill string in a first direction within a borehole extending into a subterranean formation, wherein the apparatus comprises:
a motor carried by the drill string;
a first housing operable to rotate in response to rotation of the motor;
a second housing operable to rotate in response to rotation of the first housing;
a bit operable to rotate in response to rotation of the second housing;
a joint coupled between the first and second housings and operable to orient the bit relative to the motor;
a sleeve surrounding part of the first housing and operable to remain rotationally fixed relative to the borehole during rotation of the first housing;
a cam member positioned in an internal chamber defined by the sleeve and the first housing; and
linear actuators coupled between the sleeve and the cam member; and
lengthening the borehole in a second direction angularly offset from the first direction by:
operating the linear actuators to adjust an orientation of the cam member relative to the sleeve; and
operating the motor to impart rotary motion to the first housing about a first axis parallel to the first direction, which imparts rotary motion to the second housing about a second axis parallel to the second direction, which imparts rotation motion to the bit about the second axis, wherein:
operating the linear actuators to adjust the orientation of the cam member relative to the sleeve causes reciprocation of follower pistons engaged by the cam member;
reciprocation of the follower pistons causes reciprocation of drive pistons within second bores;
reciprocation of the drive pistons causes reciprocation of push rods extending between the drive pistons and the second housing; and
reciprocation of the push rods causes the angular offset between the first and second directions.

14. The method of claim 13 wherein the follower pistons reciprocate within first bores of the first housing, wherein the drive pistons reciprocate within second bores of the first housing, and wherein the second bores are larger in diameter than the first bores.

* * * * *